(12) United States Patent
Kim et al.

(10) Patent No.: US 11,298,049 B2
(45) Date of Patent: Apr. 12, 2022

(54) METHOD AND DEVICE FOR DETECTING DANGEROUS SITUATION

(71) Applicant: SAMSUNG ELECTRONICS CO., LTD., Suwon-si (KR)

(72) Inventors: Joon-Ho Kim, Seongnam-si (KR); Joo-Young Kim, Suwon-si (KR); Hyun-Jae Baek, Seoul (KR); Do-Jun Yang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/139,807

(22) Filed: Sep. 24, 2018

(65) Prior Publication Data
US 2019/0090786 A1  Mar. 28, 2019

(30) Foreign Application Priority Data

Sep. 27, 2017 (KR) .................. 10-2017-0125408

(51) Int. Cl.
*A61B 5/11* (2006.01)
*G06K 9/00* (2006.01)
(Continued)

(52) U.S. Cl.
CPC .......... *A61B 5/1117* (2013.01); *A61B 5/0022* (2013.01); *G06K 9/00771* (2013.01);
(Continued)

(58) Field of Classification Search
CPC combination set(s) only.
See application file for complete search history.

(56) References Cited

U.S. PATENT DOCUMENTS

| 7,110,569 B2 * | 9/2006 | Brodsky ............ G06K 9/00335 348/169 |
| 9,865,176 B2 * | 1/2018 | Tran .................. G09B 19/0092 |

(Continued)

FOREIGN PATENT DOCUMENTS

| KR | 10-2013-0032856 A | 4/2013 |
| KR | 10-2014-0106883 A | 9/2014 |

(Continued)

OTHER PUBLICATIONS

International Search Report (PCT/ISA/210) and Written Opinion (PCT/ISA/237) dated Dec. 31, 2018 issued by the International Searching Authority in International Application No. PCT/KR2018/011444.

(Continued)

*Primary Examiner* — Jeffery A Williams
(74) *Attorney, Agent, or Firm* — Sughrue Mion, PLLC

(57) ABSTRACT

A method includes obtaining, by a device and from a dynamic vision sensor (DVS), a set of images of an object that identifies that the object has moved. The method includes determining, by the device, that the object is associated with a predetermined posture based on the set of images. The method includes determining, by the device, a group to which the object belongs based on an attribute of the object and an attribute of the group. The method includes determining, by the device, whether the object is associated with the dangerous situation based on identifying that the object is associated with the predetermined posture and based on setting information associated with the group to which the object belongs.

16 Claims, 14 Drawing Sheets

(51) Int. Cl.
*G06T 7/00* (2017.01)
*A61B 5/00* (2006.01)
*G06T 7/20* (2017.01)
*G06N 3/08* (2006.01)
*G06N 20/00* (2019.01)

(52) U.S. Cl.
CPC ............... *G06N 3/08* (2013.01); *G06N 20/00* (2019.01); *G06T 7/20* (2013.01)

(56) References Cited

U.S. PATENT DOCUMENTS

| | | | |
|---|---|---|---|
| 10,229,489 B1* | 3/2019 | Rush | G06K 9/6267 |
| 2007/0159332 A1* | 7/2007 | Koblasz | G06F 19/3418 |
| | | | 340/572.1 |
| 2008/0193010 A1* | 8/2008 | Eaton | G06K 9/00771 |
| | | | 382/159 |
| 2015/0109442 A1* | 4/2015 | Derenne | G06F 19/00 |
| | | | 348/143 |
| 2015/0194034 A1 | 7/2015 | Shim et al. | |
| 2016/0009279 A1 | 1/2016 | Jimaa et al. | |
| 2017/0061763 A1* | 3/2017 | Hanson | A61B 5/0077 |
| 2017/0140631 A1* | 5/2017 | Pietrocola | G08B 31/00 |
| 2018/0039745 A1* | 2/2018 | Chevalier | G16H 30/40 |
| 2018/0114063 A1* | 4/2018 | Wexler | G06K 9/00671 |
| 2019/0192052 A1* | 6/2019 | Weffers-Albu | G16H 40/63 |
| 2019/0313948 A1* | 10/2019 | Matsunaga | G08B 21/0476 |

FOREIGN PATENT DOCUMENTS

| | | |
|---|---|---|
| KR | 10-1438002 B1 | 9/2014 |
| KR | 10-2017-0037416 A | 4/2017 |
| KR | 10-1773898 B1 | 9/2017 |

OTHER PUBLICATIONS

Communication dated Sep. 10, 2020 issued by the European Patent Office in European Application No. 18860028.2.

* cited by examiner

METHOD AND DEVICE FOR DETECTING DANGEROUS SITUATION

CROSS-REFERENCE TO RELATED APPLICATION(S)

This application is based on and claims priority under 35 U.S.C. § 119 to Korean Patent Application No. 10-2017-0125408, filed on Sep. 27, 2017, in the Korean Intellectual Property Office, the disclosure of which is incorporated by reference herein in its entirety.

BACKGROUND

1. Field

The disclosure relates to a method and a device for detecting a dangerous situation (e.g., a fall) according to profile information of an object using a dynamic vision sensor (DVS).

2. Description of Related Art

The development of medical technology is leading to an aging society with an extended life expectancy. Accordingly, the importance of elderly health is increasing. Falls which result in bodily injury occur mainly in the elderly, but may occur in all ages. In particular, falls among the elderly are increasing and may lead to serious injury or death. More than one-third of Americans aged 65 or older experience falls more than once a year.

In addition to death due to falls, falls among the elderly result in a significant decrease in quality of life due to severe injuries. Twenty to thirty percent of elderly people who are treated at a hospital for falls suffer from bruises, hip fractures, or head damage due to falls. Falls are the biggest cause of elderly trauma and are expected to continue to increase with the increase in the elderly population.

Falling may happen to anyone, but the severity of falls may vary depending on age, individual, and sex. For example, even if people fall at the same pace, there is a difference in the degree of severity between a situation in which a young healthy person falls and a situation in which an unhealthy person or an elderly person falls.

Therefore, there is a need for a system that accurately detects the presence or absence of a fall in accordance with profile information of a user, and accurately predicts a danger level due to the fall.

SUMMARY

Provided are a method and a device for detecting a dangerous situation (e.g., a fall) according to profile information of an object using a dynamic vision sensor (DVS).

Additional aspects will be set forth in part in the description which follows and, in part, will be apparent from the description, or may be learned by practice of the presented embodiments.

In accordance with an aspect of the disclosure, a method of detecting a dangerous situation includes: obtaining, by a device and from a dynamic vision sensor (DVS), a set of images of an object that identifies that the object has moved; determining, by the device, that the object is associated with a predetermined posture based on the set of images; determining, by the device, a group to which the object belongs based on an attribute of the object and an attribute of the group; and determining, by the device, whether the object is associated with the dangerous situation based on identifying that the object is associated with the predetermined posture and based on setting information associated with the group to which the object belongs.

In accordance with another aspect of the disclosure, a dangerous situation detection device includes: a dynamic vision sensor (DVS) configured to obtain a set of images of an object that identifies that the object has moved; a memory configured to store one or more instructions; and a processor configured to execute the one or more instructions to: determine, based on the set of images, that the object is associated with a posture; determine a group to which the object belongs based on an attribute of the group and an attribute of the object; and determine whether the object is associated with the dangerous situation based on identifying that the object is associated with the posture and based on setting information associated with the group to which the object belongs.

In accordance with another aspect of the disclosure, a computer program product comprising a computer-readable storage medium comprising instructions that, when executed by one or more processors, cause the one or more processors to: obtain, from a dynamic vision sensor (DVS), a set of images of an object that identifies that the object has moved; determine that the object is associated with a posture based on the set of images; determine a group to which the object belongs based on an attribute of the group and an attribute of the object; and determine whether the object is in a dangerous situation based on the object being associated with the posture and based on setting information of the group.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
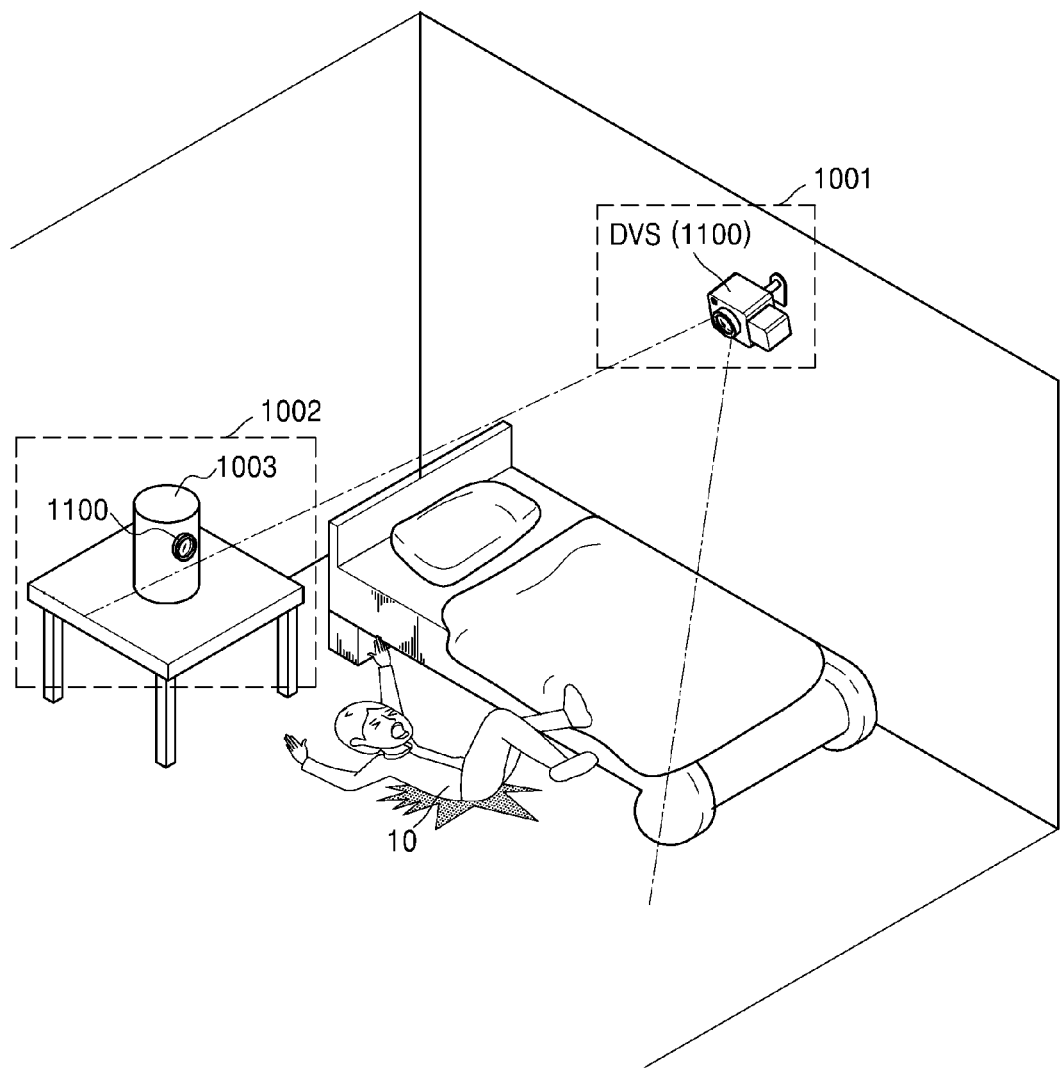
FIG. 1 is a view for explaining an operation of a dangerous situation detection device according to an embodiment.

Terms used in the disclosure will be briefly described, and the present embodiment will be described in detail.

General and widely used terms have been employed herein, in consideration of functions provided in the disclosure, and may vary according to an intention of one of ordinary skill in the art, a precedent, or emergence of new technologies. Additionally, in some cases, an applicant may arbitrarily select specific terms, in which case, the applicant will provide the meaning of the terms in the description of the embodiments. Accordingly, it will be understood that the terms used herein should be interpreted as having a meaning that is consistent with their meaning in the context of the relevant art and will not be interpreted in an idealized or overly formal sense unless expressly so defined herein.

Throughout the specification, when a portion "includes" an element, another element may be further included, rather than excluding the existence of the other element, unless otherwise described. In addition, terms such as " . . . unit", " . . . module", or the like refer to units that perform at least one function or operation, and the units may be implemented as hardware or software or as a combination of hardware and software.

In the specification, the term "fall" may refer to an event in which a specific object (e.g., a person) falls and is injured.

Below, a detailed description of embodiments of the disclosure will be provided with reference to attached drawings such that one with an ordinary skill in the art may easily perform embodiments. In this regard, the present disclosure may have different forms and should not be construed as being limited to the descriptions set forth herein. In addition, descriptions of well-known functions and constructions will be omitted for clarity and conciseness, and similar reference numerals are assigned to similar elements throughout the specification.

FIG. 1 is a view for explaining an operation of a dangerous situation detection device according to an embodiment.

Referring to FIG. 1, a dangerous situation detection system according to an embodiment may include a dangerous situation detection device. A dangerous situation may mean that a movable object (e.g., a person or animal) is in a dangerous situation. For example, the dangerous situation may vary, such as an object falling, a fire in a space where an object is, floods, landslides, and gas leaks. Hereinafter, the case where an object falls will be described as an example of the dangerous situation for convenience of explanation.

According to an embodiment, a dangerous situation detection device 1000 may be a device that obtains at least one image (frame) for an object 10 and detects a fall of the object 10 using at least one obtained image (frame). According to an embodiment, the object 10 may be a person, an animal, or the like, but is not limited thereto. According to an embodiment, a fall detection system may designate a detection target as a specific object based on a user's input. For example, the fall detection system may only specify people, not animals, as a target of fall detection. In addition, the fall detection system may designate a specific person as a monitoring target. For example, when a mother, a father, a grandfather, and a child are together at home, the grandfather may be designated as a target of fall detection.

According to an embodiment, the dangerous situation detection device 1000 may be installed in a fixed position. According to an embodiment, the dangerous situation detection device 1000 may be implemented in the form of a surveillance camera 1001. The dangerous situation detection device 1000 implemented in the form of the surveillance camera 1001 may be fixedly installed at a predetermined position. The dangerous situation detection device 1000 implemented in the form of the surveillance camera 1001 may be attached to walls, ceilings, furniture, and the like inside the house. The dangerous situation detection device 1000 implemented in the form of the surveillance camera 1001 may provide information on installed locations. According to an embodiment, the dangerous situation detection device 1000 may be movable. The dangerous situation detection device 1000 may be included in movable accessories, furniture, electronics, interior products, and the like. According to an embodiment, the dangerous situation detection device 1000 may be implemented as a movable (portable) device 1002 coupled to a speaker 1003. The dangerous situation detection device 1000 implemented in the movable device 1002 may be variably located in an area where a dangerous situation may occur. The dangerous situation detection device 1000 implemented in the movable device 1002 may be installed on a bed, a staircase, a threshold, or the like where a fall may occur.

According to an embodiment, the dangerous situation detection device 1000 may include a dynamic vision sensor (DVS) 1100. According to an embodiment, the dangerous situation detection device 1000 implemented in the form of a surveillance camera 1001 and the dangerous situation detection device 1000 implemented in the movable device 1002 may include the DVS 1100. According to an embodiment, the dangerous situation detection device 1000 implemented in the movable device 1002 may include the DVS 1100 configured to obtain image data for moving objects with other functions (e.g., an AI speaker function).

The DVS 1100 may be an image sensor that adopts a method of receiving information of a person's iris and may be a sensor capable of obtaining image data of a moving object. For example, the DVS 1100 may transmit image data to a processor only when there is a local change by motion in pixel units. That is, the DVS 1100 may transmit image data to the processor only when a motion event occurs. Accordingly, the DVS 1100 might not process data when an object is stopped, and instead might measure the moving object only when the object moves, and transmits the data to the processor. Therefore, it is possible to prevent the waste of data caused by general image sensors continuing to send frames to the processor.

The DVS 1100 may solve a problem of general visual recognition systems that are vulnerable to rapid motion. The DVS 1100 may overcome a blur phenomenon because the DVS 1100 receives data on a per-pixel basis rather than on a frame-by-frame basis.

Also, the DVS 1100 may have a resolution in microseconds. In other words, the DVS 1100 may have a better time resolution (e.g., a super-fast frame>1 K FPS) than a super high-speed camera that shoots thousands of frames per second. In addition, power consumption and data storage requirements of the DVS 1100 have also been greatly reduced, resulting in a dramatic increase in a dynamic range (a range of brightness that the DVS 1100 can distinguish).

Since an image obtained by the DVS 1100 might represent only an outline of the moving object 10, it may also be useful for protecting privacy of the monitored object 10. Furthermore, the DVS 1100 may detect motions of the object 10 only with a slight amount of light even in a dark place.

According to an embodiment, the DVS 1100 may periodically obtain an image, and the dangerous situation detection device 1000 may monitor whether the object 10 falls based on the image periodically obtained in the DVS 1100. For example, when the object 10 falls off the bed, the DVS 1100 may detect motion of the object 10 falling from the bed. Here, the dangerous situation detection device 1000 may efficiently determine whether the object 10 falls by using a plurality of deep learning models step by step. For example, the dangerous situation detection device 1000 may reduce consumption of computational resources by analyzing a video only when a static image includes the object 10 in the posture related to the fall, instead of analyzing the video from the beginning. An operation of the dangerous situation detection device 1000 to determine whether the object 10 falls according to a profile of the object 10 will be described in detail later below.

According to an embodiment, a fall detection system may further include a server. In this case, the server may receive fall detection information of the object 10 from the dangerous situation detection device 1000. The server may verify the received fall detection information, or may transmit a warning message to an external device according to the fall detection information.

According to an embodiment, the dangerous situation detection device 1000 may directly generate deep learning models for confirming whether or not a fall occurs, or may receive the deep learning models from the server. The deep learning models may be, but are not limited to, a supervised learning model, an unsupervised learning model, and a reinforcement learning model. The dangerous situation detection device 1000 may apply images collected from the DVS 1100 to the deep learning models to determine whether the object 10 falls. According to an embodiment, the dangerous situation detection device 1000 may request the server to determine whether the object 10 falls, while transmitting the images collected from the DVS 1100 to the server. For convenience of description, a case where the fall detection system does not include the server will be described first as an example.

Figure 2:
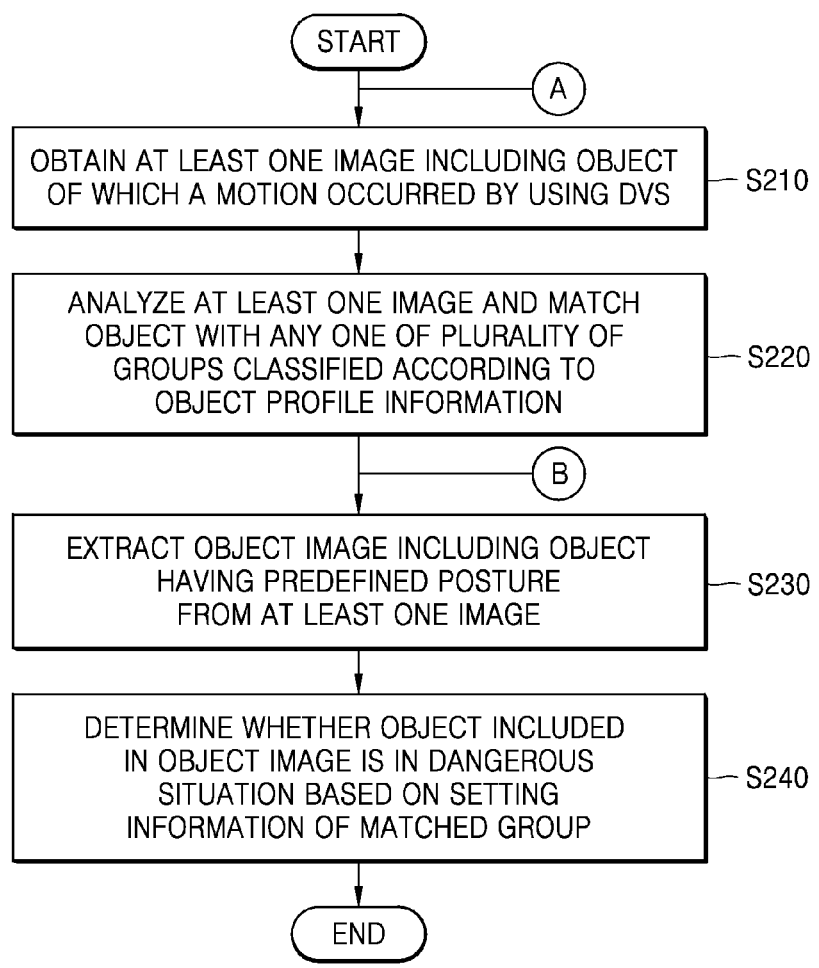
FIG. 2 is a flowchart illustrating a method of detecting a fall based on a user profile according to an embodiment.

FIG. 2 is a flowchart illustrating a method of detecting a fall based on a user profile according to an embodiment.

In operation S210, the dangerous situation detection device 1000 according to an embodiment may obtain at least one image including an object of which a motion occurred by using the DVS 1100. According to an embodiment, the DVS 1100 may be installed in a home, office, or hospital, but is not limited thereto. The dangerous situation detection device 1000 may be installed outdoors. For example, the dangerous situation detection device 1000 may be installed in a mountain where a fall accident occurs frequently.

According to an embodiment, a movable object may be a person to be monitored. When the object moves, the DVS 1100 may capture an image of the object. The image of the object may include an outline, an edge, a silhouette of the object, or other information associated with the object.

In operation S220, the dangerous situation detection device 1000 according to an embodiment may analyze at least one image and match the object with any one of a plurality of groups classified according to object profile information.

According to an embodiment, the "object profile information" may be information including characteristics of the object. The object profile information may be information for identifying the object. The object profile information may include gender, age group, living area, lesion, walking speed, momentum, and/or the like.

According to an embodiment, the "group" may be classified by a plurality of pieces of object profile information obtained by observing a plurality of objects. According to an embodiment, the group may be classified based on any one of the plurality of pieces of object profile information. According to an embodiment, the group may be classified according to a reference obtained by combining the plurality of pieces of profile information.

For example, the group may be formed into a plurality of groups by classifying them based on age into groups divided according to every 10 years. For example, an infant group from 0 to 10 years old and an elderly group from 71 to 90 years old may be defined. Further, as another example, the group may be classified by a value calculated by weighting the plurality of pieces of profile information. For example, a "group of elderly men with a herniated lumbar disc" may be determined based on object profile characteristics such as 70s, male, and curved waist.

A method of determining the plurality of groups is not limited. According to an embodiment, the plurality of groups may be classified by an artificial intelligence (AI) learning model. According to an embodiment, the plurality of groups may be classified according to classification criteria input by a user.

In operation S230, the dangerous situation detection device 1000 according to an embodiment may extract an object image including an object having a predefined posture from at least one image. The dangerous situation detection device 1000 may detect the object image including an object having a predefined posture from at least one image. Each of the at least one image may be a static image.

According to an embodiment, the static image refers to each image of a plurality of continuous images measured while moving. According to an embodiment, the static image refers to any one of a plurality of images included in a user's motion image obtained by the DVS 1100.

According to an embodiment, the dangerous situation detection device 1000 may analyze at least one image obtained by the DVS 1100 one by one using a deep learning model. The deep learning model may be a trained model for analyzing a static image and detecting an image including an object having a predefined posture.

The predefined posture may be a posture related to a fall. According to an embodiment, the predefined posture may be a posture in which a particular body part (e.g., head, back, chest, knee, heel, palm, etc.) is in contact with the floor (or stairs). For example, the predefined posture may be, but is not limited to, a lying posture on the floor, a bowed posture on the floor, a lying posture on the side, a leaning posture on the stairs, and the like.

For example, when a grandfather falls out of bed, the dangerous situation detection device 1000 may analyze images one by one using the deep learning model, and then detect an image including the grandfather lying on the floor.

According to an embodiment, the dangerous situation detection device 1000 may compensate for a shape or size of an object included in a static image before analyzing the static image using the deep learning model. For example, the dangerous situation detection device 1000 may compensate for a shape or size of an object included in at least one image in consideration of at least one of an angle and a position of the DVS 1100, and may compare a posture of the object whose shape or size is compensated for with the predefined posture.

According to an embodiment, when an object image including an object having a posture related to a fall is detected, the dangerous situation detection device 1000 may analyze a series of images (e.g., accumulated frames for a certain period of time) to obtain information on a first motion change of the object in order to accurately determine whether the object is in a fall state. For example, when an image (e.g., $n^{th}$ frame) of an object lying on the floor and out of bed is detected, the dangerous situation detection device 1000 may analyze the accumulated images (e.g., $(n-10)^{th}$ frame to $(n+10)^{th}$ frame) for a certain period of time and detect a motion change of the object falling from the bed to the floor. Also, the dangerous situation detection device 1000 may detect a motion change of the object after the body touches the floor.

In operation S240, the dangerous situation detection device 1000 according to an embodiment may determine, based on setting information of a matched group, whether the object included in the object image is in a dangerous situation. The dangerous situation detection device 1000 may determine whether the object is in a fall state based on setting information of a group matched with the object and information on a motion change of the object.

According to an embodiment, when a degree of similarity between the motion change of the object and a motion change representing a pre-stored fall is greater than a threshold value (e.g., 90%), the dangerous situation detection device 1000 may determine a state of the object as a fall state.

According to an embodiment, the "motion change representing a pre-stored fall" may be set according to the setting information of a group matched with the object. According to an embodiment, motion representing a fall may be determined according to profile information of a user. For example, a motion change such as falling speed, fallen shape, shape of limb, etc., which represents a fall of an elderly person in his or her 80s, may be set differently from a motion change of a teenager.

When a degree of similarity between the motion change of the object and the motion change representing a pre-stored fall is less than a threshold value (e.g., 90%), the dangerous situation detection device 1000 may determine a state of the object as not a fall state.

For example, when the motion change of the object is similar to a motion pattern due to a fall (e.g., when the object can no longer move after falling from the bed to the floor), the dangerous situation detection device 1000 may determine a state of the object as a fall state. However, when the motion change of the object is different from the motion pattern due to a fall (e.g., when the object slides off the bed, with hips and palms touching the floor, but is then able to get up and walk right away), the dangerous situation detection device 1000 may determine a state of the object as not a fall state.

Figure 3:
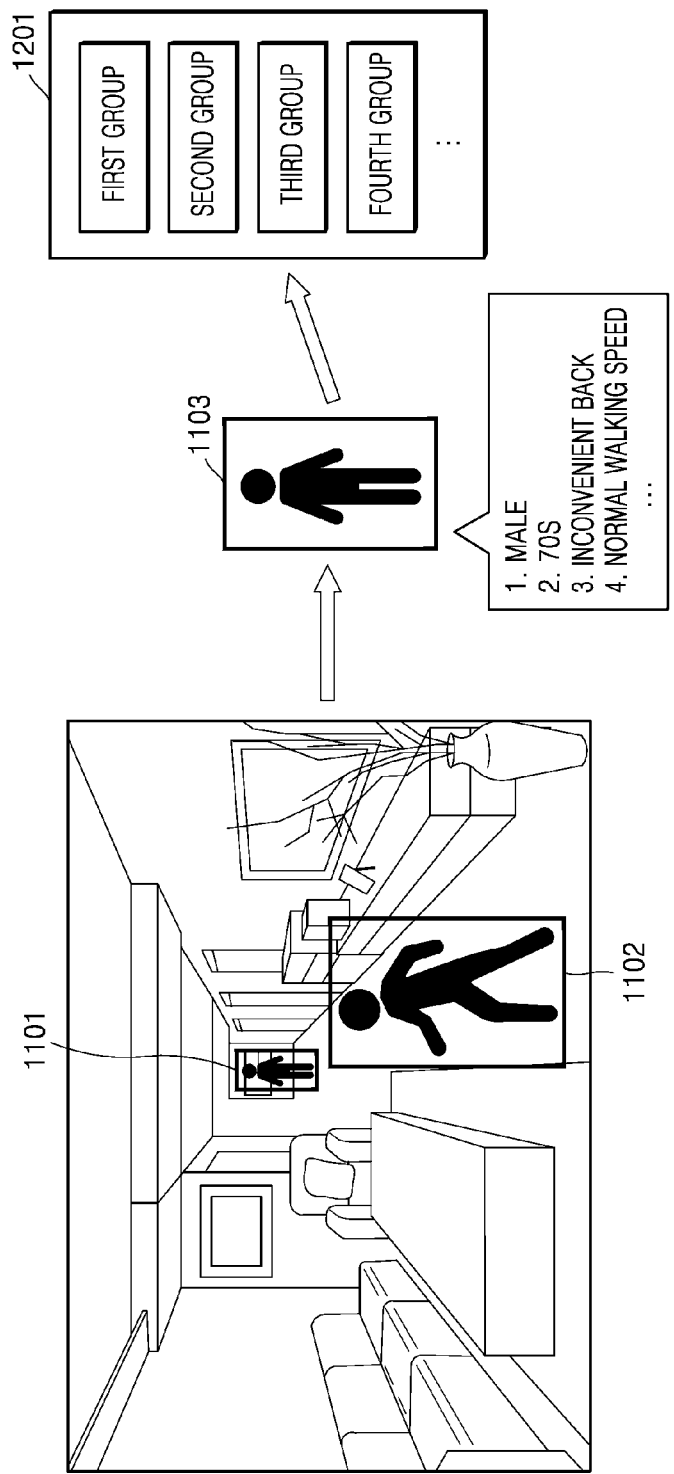
FIG. 3 is a view for explaining an operation of analyzing object information according to an embodiment and matching an object with one of a plurality of groups.

FIG. 3 is a view for explaining an operation of analyzing object information according to an embodiment and matching an object with one of a plurality of groups.

As shown in FIG. 3, the dangerous situation detection device 1000 may obtain a plurality of images 1101 and 1102 including a moving object. According to an embodiment, the plurality of images 1101 and 1102 may be obtained by imaging an object with motion. The plurality of images 1101 and 1102 may be obtained in all situations, such as a dangerous situation and a general situation.

According to an embodiment, the dangerous situation detection device 1000 may analyze the plurality of images 1101 and 1102 including the object to obtain behavior of the object. According to an embodiment, the dangerous situation detection device 1000 may obtain object profile information from an image 1103 of the object. For example, the object profile information is related to a male estimated to be in his 70s, and having backache, walking at normal walking speed, and so on. According to an embodiment, the dangerous situation detection device 1000 may analyze a plurality of images of the object to obtain a plurality of pieces of profile information.

According to an embodiment, the dangerous situation detection device 1000 may analyze characteristics of the object from the plurality of pieces of profile information. For example, the dangerous situation detection device 1000 may analyze the plurality of pieces of profile information to determine gender, age group, and physical characteristics of the object. The dangerous situation detection device 1000 may map a group including characteristics most similar to the object based on the obtained object profile information. The dangerous situation detection device 1000 may match any one of a plurality of groups 1201 classified by the object profile information with the object.

According to an embodiment, each of the plurality of groups may include separate group setting information. The group setting information may include information on a virtual model generalized to determine a situation of the object.

Figure 4:
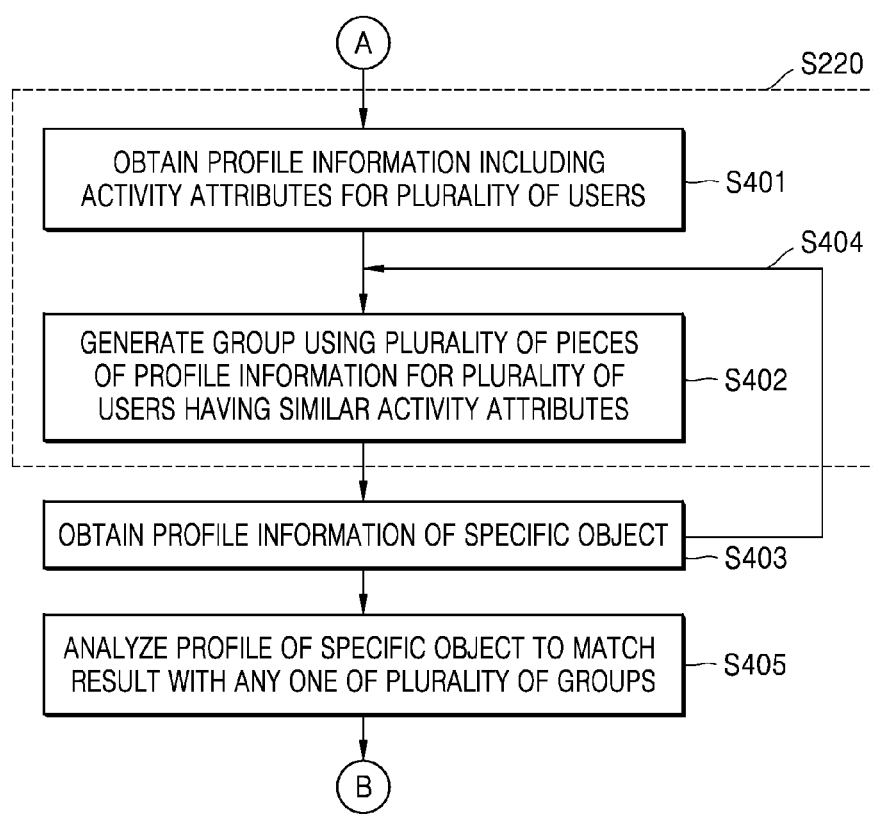
FIG. 4 is a view for explaining an operation of creating a plurality of groups according to an embodiment and matching objects and the groups.

FIG. 4 is a view for explaining an operation of creating a plurality of groups according to an embodiment and matching objects and the groups.

In operation S401, the dangerous situation detection device 1000 according to an embodiment may obtain profile information including activity attributes for a plurality of users. According to an embodiment, the dangerous situation detection device 1000 may obtain the plurality of pieces of profile information for the plurality of users. According to an embodiment, the dangerous situation detection device 1000 may obtain object profile information from a DVS sensor. Also, the dangerous situation detection device 1000 may obtain the object profile information through a wearable device, a user terminal, an external device, and a server. For example, when a user wears a wearable device, information on user activity such as user profile information, an average walking speed, and the number of steps during a day may be obtained from the wearable device.

In operation S402, the dangerous situation detection device 1000 may generate a group using the plurality of pieces of profile information for the plurality of users having similar activity attributes. The dangerous situation detection device 1000 may analyze the object profile information to generate a plurality of users having similar activity attributes as a group. The dangerous situation detection device 1000 may determine setting information for determining a dangerous situation of an object matched with the group. For example, the dangerous situation detection device 1000 may generate virtual models as a criterion for determining in what situations the object is in danger. The dangerous situation detection device 1000 may designate each of the virtual models as a plurality of groups. For example, the first virtual model may be mapped to a first group, and the second virtual model may be mapped to a second group. For example, the first virtual model may be a 70s male model with knee pain, and the second virtual model may be an 80s female model with a waist disk.

Profile information may include gender, age, lesion, normal activity, walking speed, activity pattern, stride, and whether an auxiliary device is installed. The setting information may be average information of profile information for a plurality of users used to generate a group.

According to an embodiment, operations S401 and S402 may be included in operation S220 of FIG. 2.

In operation S403, the dangerous situation detection device 1000 according to an embodiment may obtain profile information of a specific object. According to an embodiment, the dangerous situation detection device 1000 may use the DVS 1100 to obtain at least one image including a movable object.

According to an embodiment, the movable object may be a person or an animal to be monitored. When the object moves, the DVS 1100 may capture an image of the object. Here, the image of the object may include an outline, an edge, or a silhouette of the object.

When the object moves and other objects move together, the image of the object may show an outline of the other objects as well as the outline of the object. For example, if an object rides on a wheelchair and collapses with a wheelchair, an object image may show both an outline of the object and an outline of the wheelchair.

In operation S404, the dangerous situation detection device 1000 according to an embodiment may update group setting information using the obtained object profile information. According to an embodiment, by updating the group setting information using the continuously obtained profile information of the object, a group mapped to a model closest to the object may be set.

In operation S405, the dangerous situation detection device 1000 may analyze a profile of a specific object to match the result with any one of a plurality of groups. For example, when the dangerous situation detection device 1000 analyzes the obtained object profile information and determines that the object is an elderly male with knee pain, the object may be matched with the first group having setting information of the 70s male model with knee pain. Setting information of a group matched with an object may be utilized as reference information for detecting a dangerous situation of the object later below.

Figure 5:
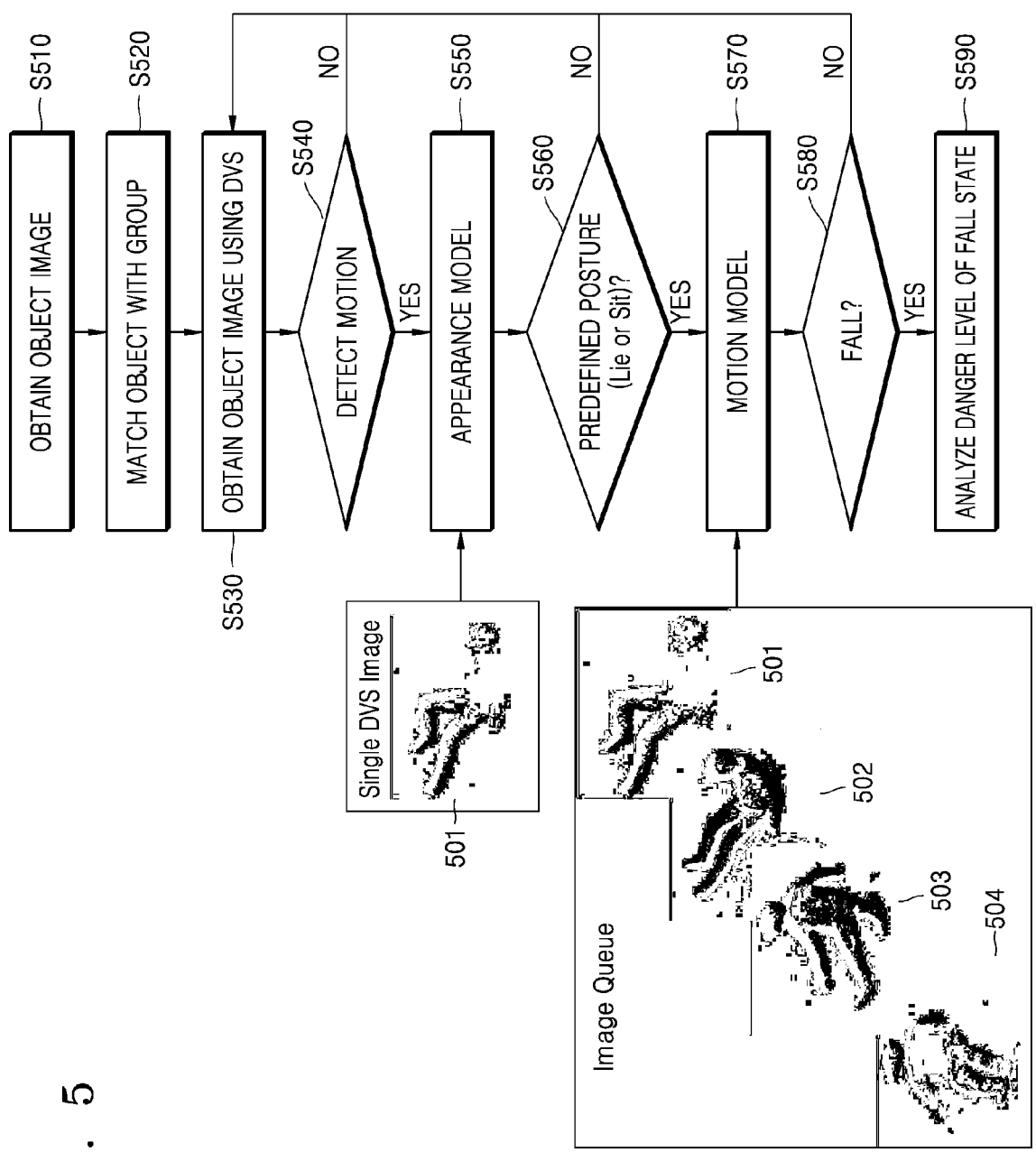
FIG. 5 is a flowchart illustrating a method of adjusting an image acquisition mode depending on whether object motion is detected according to an embodiment.

FIG. 5 is a flowchart illustrating a method of adjusting an image acquisition mode depending on whether object motion is detected according to an embodiment.

In operation S510, the dangerous situation detection device 1000 according to an embodiment may obtain at least one image including a movable object using the DVS 1100 or another sensor.

In operation S520, the dangerous situation detection device 1000 according to an embodiment may match an object with a group including a model closest to the object. For example, the object may be matched with a group including information that is close to object information analyzed based on a silhouette, edge, etc. obtained by the DVS 1100.

In operation S530, the dangerous situation detection device 1000 may obtain an image of the object using the DVS 1100.

According to an embodiment, an initial image for obtaining the image of the object may vary in resolution depending on a system setting value or a user setting value. For example, the initial image may be a high-resolution image or a low-resolution image. Here, the high-resolution image may mean an image whose resolution is greater than a threshold value, and a low-resolution image may mean an image whose resolution is equal to or less than the threshold value.

According to an embodiment, the resolution may be a reference point for the DVS 1100 to detect an image of an object. For example, even if an object moves at identical intensity, the DVS 1100 may or may not detect an image of the object depending on the resolution. According to an embodiment, the resolution may be set to a low resolution/high resolution based on a system setting value or a user setting value. For example, when the object falls at an intensity of 1, the DVS 1100 may detect motion of the object at a high resolution without detecting motion of the object at a low resolution. Since the DVS 1100 may set a resolution for image detection according to characteristics of the object because the DVS 1100 may have a resolution in microseconds.

According to an embodiment, the threshold value may mean a threshold resolution that is a reference for obtaining an image by determining that the object is moving by the DVS 1100. According to an embodiment, the threshold may be set by a user or automatically set by a system.

In operation S540, the dangerous situation detection device 1000 may detect motion of the object using at least one image obtained by the DVS 1100.

For example, in the absence of a person in a room with a bed and dresser, no outline may appear on at least one image obtained by the DVS 1100. However, when a person comes into a room with a bed and a dresser, an outline of the moving person appears in at least one image obtained by the DVS 1100. Therefore, the dangerous situation detection device 1000 may detect whether an object (e.g., a person) is moving by analyzing at least one image.

If motion of an object (e.g., a person) is not detected, the dangerous situation detection device 1000 may not analyze the image anymore because there is no image obtained by the DVS 1100. Since the dangerous situation detection device 1000 obtains the image of the object only when there is motion, unnecessary consumption of computational resources may be reduced. When motion of an object (e.g., a person) is detected, the dangerous situation detection device 1000 may perform operation S580 to determine whether the motion of the object (e.g., a person) is related to a fall.

In operation S550, when motion of the object is detected, the dangerous situation detection device 1000 may analyze at least one image obtained by the DVS 1100, one by one, using an appearance model. According to an embodiment, the appearance model may be a trained model which is determined to be similar to a shape or pose of an object in a group matched with the object.

For example, the dangerous situation detection device 1000 may use an appearance model to detect an image (e.g., an image including a person lying on the floor) that includes an object of a posture related to a fall. The appearance model 1710 may be a trained model that analyzes static images one by one to detect a body shape or pose of an object included in each of the static images, and determine whether the detected body shape or pose of the object is similar to a posture related to a fall.

For example, when the grandfather enters a bathroom equipped with the DVS 1100, the DVS 1100 may detect motion of the grandfather. The DVS 1100 may sequentially transmit image frames shot from the time when the motion of the grandfather is detected to a processor of the dangerous situation detection device 1000, and the processor may analyze the sequentially transmitted image frames using the appearance model. For example, the processor may detect a grandfather's posture included in the sequentially transmitted image frames. The processor may analyze the grandfather's posture using an appearance model of a group matched with the grandfather.

If the grandfather falls on the bathroom floor, the processor of the dangerous situation detection device 1000 may detect an $n^{th}$ frame 501 including the grandfather lying on his back on the bathroom floor from among the sequentially transmitted image frames.

In operation S560, the processor of the dangerous situation detection device 1000 may determine whether postures of the object detected from the sequentially transmitted image frames are similar to a predefined posture (e.g., a lying posture). The predefined posture may be a posture defined according to setting information of a group matched with an object. For example, a posture defined according to setting information of elderly people in their 70s may be defined in consideration of the average body shape, gender, a lying position according to the lesion, a posture at the time of falling, and the like.

If the detected postures of the object are not similar to the predefined posture, the dangerous situation detection device 1000 may return to operation S530 to obtain the next image frame by the DVS 1100. If the detected postures of the object are similar to the predefined posture, the dangerous situation detection device 1000 may perform operation S570 to accurately determine whether the object falls.

For example, when an $(n-3)^{th}$ frame 504 is input, a posture of an object included in the $(n-3)^{th}$ frame 504 is not a lying posture, so that the processor of the dangerous situation detection device 1000 may return to operation S530 to obtain an $(n-2)^{th}$ frame 503 by the DVS 1100. For example, when the $(n-2)^{th}$ frame 503 is input, a posture of an object included in the $(n-2)^{th}$ frame 503 is not a lying posture, so that the processor of the dangerous situation detection device 1000 may return to operation S530 to obtain an $(n-1)^{th}$ frame 502 by the DVS 1100. For example, when the $(n-1)^{th}$ frame 502 is input, a posture of an object included in the $(n-1)^{th}$ frame 502 is not a lying posture, so that the processor of the dangerous situation detection device 1000 may return to operation S530 to obtain an $n^{th}$ frame 501 by the DVS 1100.

When the $n^{th}$ frame 501 is input, a posture of an object included in the $n^{th}$ frame 501 is a lying posture, so that the processor of the dangerous situation detection device 1000 may proceed to operation S580 to determine whether the object falls.

In operation S570, the dangerous situation detection device 1000 may detect a motion change using a motion model and determine whether the detected motion change is similar to a motion change indicating a fall.

According to an embodiment, the motion model may be a model that is trained so as to detect motion patterns of an object by analyzing a plurality of images (e.g., videos), and determine whether the detected motion patterns of the object are similar to a motion pattern indicating a fall.

According to an embodiment, since the $n^{th}$ frame 501 including the object of a lying posture is detected from operation S550 and operation S560, the dangerous situation detection device 1000 may analyze a series of images (e.g., the $(n-3)^{th}$ frame 504, the $(n-2)^{th}$ frame 503, the $(n-1)^{th}$ frame 502, and the $n^{th}$ frame 501) related to the $n^{th}$ frame 501 using the motion mode.

The dangerous situation detection device 1000 may analyze the series of images (e.g., the $(n-3)^{th}$ frame 504, the $(n-2)^{th}$ frame 503, the $(n-1)^{th}$ frame 502, and the $n^{th}$ frame 501) to detect a motion pattern in which the grandfather stands (e.g., the $(n-3)^{th}$ frame 504) on the bathroom floor and slides (e.g., the $(n-2)^{th}$ frame 5803), touches the hips on the floor (e.g., the $(n-1)^{th}$ frame 502), and then touches the back and the head on the bathroom floor (e.g., the $n^{th}$ frame 501). Here, the dangerous situation detection device 1000 may determine that the detected motion pattern of the grandfather is similar to a pre-trained motion pattern indicating a fall.

In operation S580, if the detected motion change is not similar to the motion pattern indicating a fall, the dangerous situation detection device 1000 may return to operation S530 to obtain the next image by the DVS 1100. If the detected motion change is similar to the motion change indicating a fall, the dangerous situation detection device 1000 may determine a state of the object as a fall state.

In operation S590, when a state of the object is determined as a fall state, the dangerous situation detection device 1000 may analyze a danger level of the fall state.

According to an embodiment, the dangerous situation detection device 1000 may analyze the danger level of the fall state using information such as which position the object has fallen into, and whether there is no motion after the object has fallen. According to an embodiment, the dangerous situation detection device 1000 may analyze the danger level of the fall state using information about an environment around where the object fell and time (e.g., day, night, dawn, etc.) at which the object fell.

Generally, since the motion model processes multiple images in a cumulative manner (e.g., N images stacking), the processing takes N times longer than in an appearance model that processes a single image. However, the dangerous situation detection device 1000 according to an embodiment operates the motion model only when the dangerous situation detection device 1000 recognizes a scene where the body touches the floor using the appearance model. Therefore, the dangerous situation detection device 1000 may efficiently use computational resources for fall detection.

Figure 6:
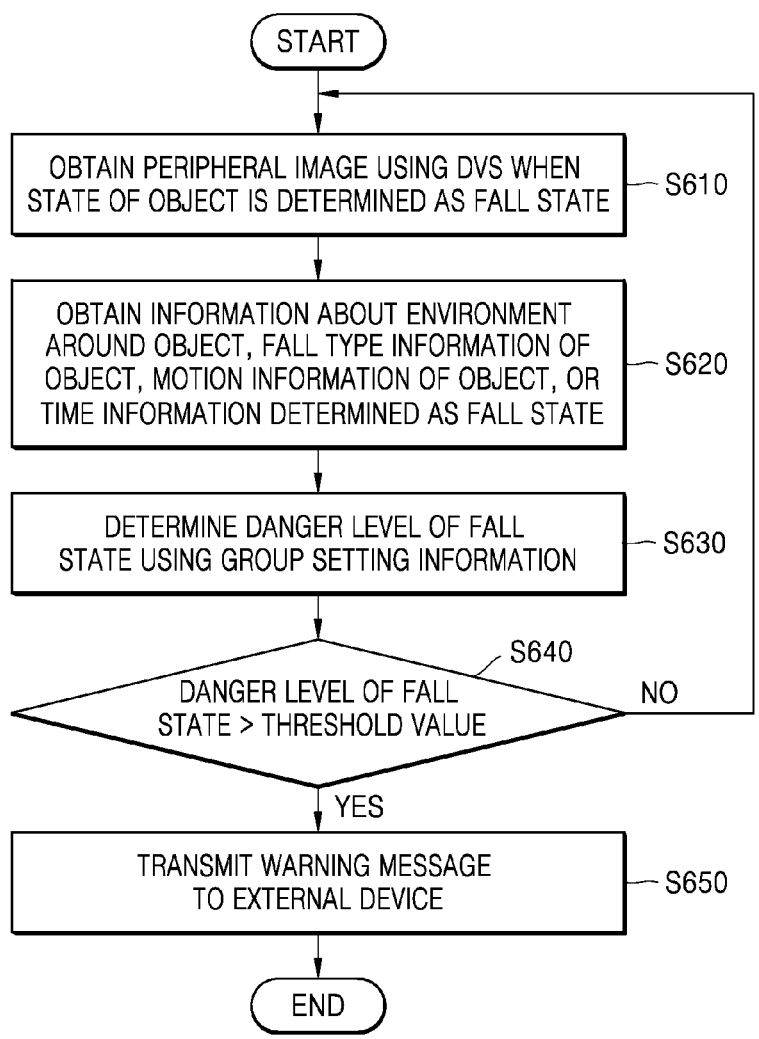
FIG. 6 is a flowchart illustrating a method of determining a danger level of a fall state according to an embodiment.

FIG. 6 is a flowchart illustrating a method of determining a danger level of a fall state according to an embodiment.

In operation S610, the dangerous situation detection device 1000 may obtain a peripheral image using the DVS 1100 when a state of the object is determined as a fall state.

In operation S620, the dangerous situation detection device 1000 may obtain information about an environment around the object, fall type information of the object, motion information of the object, or time information determined as a fall state using a surrounding image.

According to an embodiment, the dangerous situation detection device 1000 may obtain information about the environment around the object from a server, an external camera, peripheral accessories, and an external device. For example, when the dangerous situation detection device 1000 is coupled to an AI speaker, location information of the dangerous situation detection device 1000 may be obtained using a global positioning system (GPS) sensor of the AI speaker. Furthermore, when the dangerous situation detection device 1000 is fixedly installed on the wall of the bedroom, an installed location, characteristics of the installed place, and furniture arrangement of the bedroom may be input from a user. The information about the environment around the object may include information about the object around a place where the object has fallen (e.g., information about a dangerous object that exists at a place where the user has fallen, information about an object that has fallen with the user, etc.), but is not limited thereto.

According to an embodiment, the fall type information of the object may be information on how the object has fallen. For example, the fall information of the object may include, but is not limited to, information about whether the head or face touches the floor, information about whether the arm or leg is broken, and the like.

The motion information of the object may be information on motion of the object after a state of the object is determined as a fall state. For example, the motion information of the object may include, but is not limited to, a motion change value, total time information for which the motion change value remains below a threshold value, and the like.

Time information determined as a fall state may be information on what time the object fell over. For example, if it is determined that a fall has occurred at night time, time information at the time of the fall needs to be collected because the help of people nearby may be insufficient and serious situation may result.

In operation S630, the dangerous situation detection device 1000 may determine a danger level of the fall state using group setting information and information obtained from surrounding images. The danger level of the fall state may mean a degree of danger level of the object according to a fall.

According to an embodiment, the dangerous situation detection device 1000 may determine the danger level of the fall state using information about the environment around the object. For example, if there is a protrusion where the object has fallen, the dangerous situation detection device 1000 may determine the danger level of the fall state to be high or adjust a danger level upward. In addition, when a material of a floor where the body falls is a slippery material with moisture, the dangerous situation detection device 1000 may determine the danger level of the fall state to be high or adjust the danger level upward.

Furthermore, according to an embodiment, the dangerous situation detection device 1000 may determine the danger level of the fall state using time information of the fall state. For example, if a fall occurs between 12:00 am to 5:00 am, the dangerous situation detection device 1000 may determine the danger level of the fall state to be high or adjust the danger level upward.

In addition, the dangerous situation detection device 1000 may determine the danger level of the fall state based on the group setting information. For example, since a danger level of a posture of a young man in his 20's sitting down is different from that of a posture of an elderly man in his 70's sitting down slowly, a dangerous situation may be more accurately determined based on setting information of a group matched with the object.

According to an embodiment, the dangerous situation detection device 1000 may determine the danger level of the fall state using the fall type information of the object. For example, if the object hits the floor from head when the object falls, the dangerous situation detection device 1000 may determine the danger level of the fall state to be high. Alternatively, if the leg is twisted when the object falls, the dangerous situation detection device 1000 may determine the danger level of the fall state to be high.

According to an embodiment, the dangerous situation detection device 1000 may determine the danger level of the fall state using the motion information of the object. According to an embodiment, if the motion of the object is less than the threshold value for a certain period of time, the dangerous situation detection device 1000 may raise the danger level of the fall state. For example, if there is little motion for more than five minutes after the object is determined to have fallen, the dangerous situation detection device 1000 may raise the danger level of the fall state by three levels.

According to an embodiment, the dangerous situation detection device 1000 may combine at least two pieces of information among information about the environment around the object, fall type information of the object, motion information of the object, and time information determined as a fall state to determine the danger level of the fall state.

According to an embodiment, the dangerous situation detection device 1000 may determine the danger level of the fall state in consideration of personal information (e.g., age, physical activity ability, disease, etc.) of the object. Here, the personal information may be obtained from a user's mobile device, directly input from a user, or obtained through analysis by the DVS 1100. For example, if the object is a 10-year-old healthy student, the dangerous situation detection device 1000 may determine a danger level weight of the fall state as −3. If the object is an elderly person aged 80 years with an uncomfortable mobility and high blood pressure, the dangerous situation detection device 1000 may determine the danger level weight of the fall state as +5.

In operation S640 and operation S650, the dangerous situation detection device 1000 may transmit a warning message to an external device when the danger level of the fall state is greater than the threshold value.

For example, the dangerous situation detection device 1000 may transmit a warning message (e.g., a first user has fallen off the stairs and has been unable to move for 2 minutes) including information indicating that the object has fallen, information about the environment around the object, time information about when the motion of the object remains below a threshold value, and the like to a predetermined external device (e.g., a family device, a medical institution server, an emergency rescue request server, etc.).

Figure 7:
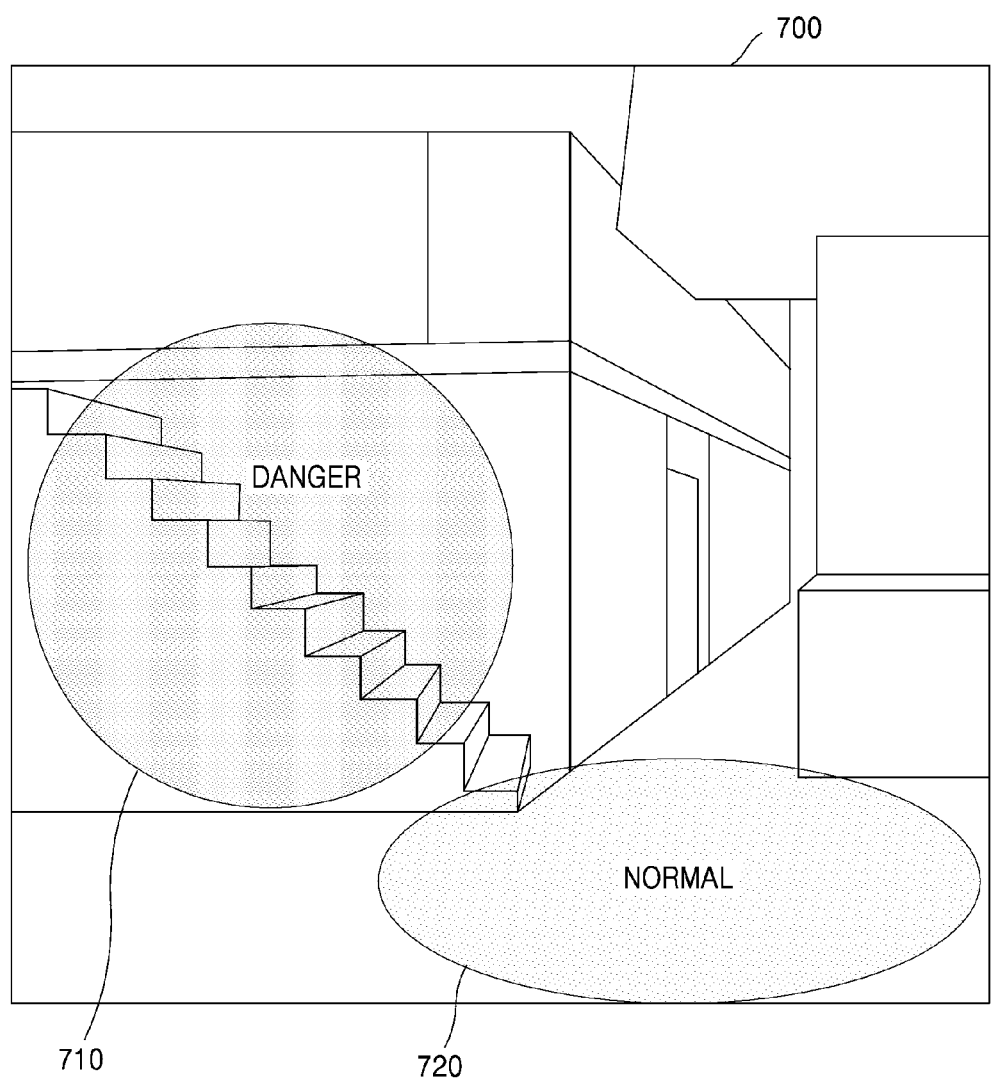
FIG. 7 is a view illustrating an operation of setting a danger level of information about an environment around a location of a dynamic vision sensor (DVS) installed in a room according to an embodiment.

FIG. 7 is a view illustrating an operation of setting a danger level of information about an environment around a location of a DVS installed in a room according to an embodiment.

Referring to FIG. 7, the dangerous situation detection device 1000 may be installed in the house. The dangerous situation detection device 1000 may generate a fall-danger-level map 600 designating a danger level of a step region 710 as 'high' and a danger level of a living room floor 720 as 'normal'.

According to an embodiment, the dangerous situation detection device 1000 may quickly determine a fall danger level in consideration of the fall-danger-level map 600 when a fall occurs. For example, the dangerous situation detection device 1000 may raise the fall danger level by two steps when a fall occurs in the step region 710.

Figure 8:
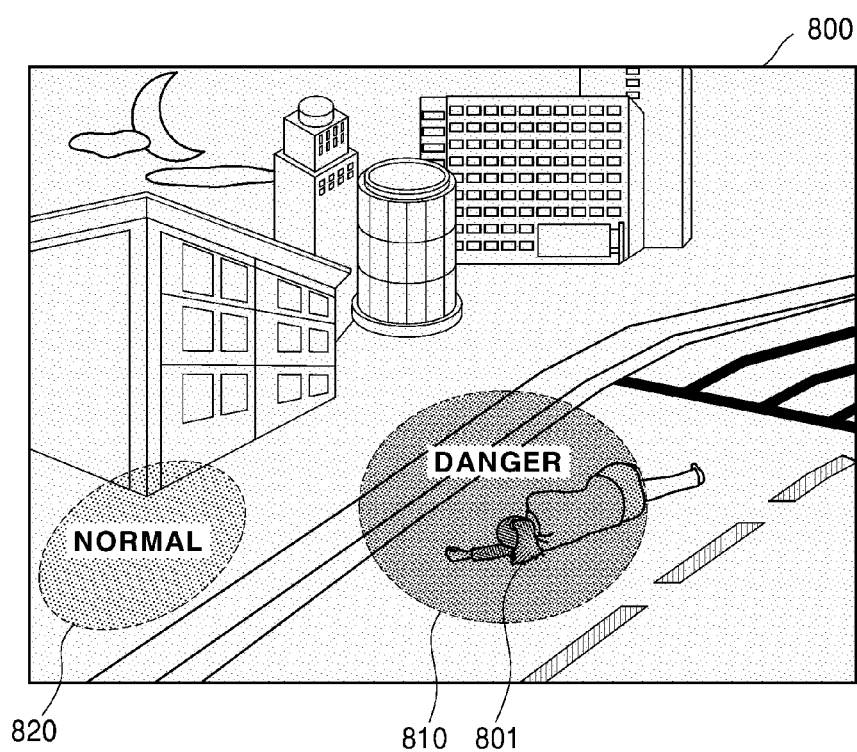
FIG. 8 is a view illustrating an operation of setting a danger level of information about an environment around a location of a DVS installed outdoors according to an embodiment.

FIG. 8 is a view illustrating an operation of setting a danger level of information about an environment around a location of a DVS installed outdoors according to an embodiment.

Referring to FIG. 8, the dangerous situation detection device 1000 may be installed to photograph outdoors, for example, a high pavement. The dangerous situation detection device 1000 may set the danger level according to surrounding environment and the time photographed. The dangerous situation detection device 1000 may generate a fall-danger-level map 800 designating a danger level of a pavement 810 that connects a road to a sidewalk as 'danger' and a danger level of a sidewalk 820 as 'normal'.

According to an embodiment, the dangerous situation detection device 1000 may quickly determine a fall danger level in consideration of the fall-danger-level map 800 when a fall occurs. For example, the dangerous situation detection device 1000 may raise the fall danger level by two steps when a fall occurs in the pavement 810. Furthermore, the fall danger level may be adjusted according to a time zone when a fall occurs. For example, if a fall occurs between 3 am and 4 am, the fall danger level may be raised by three steps.

Figure 9:
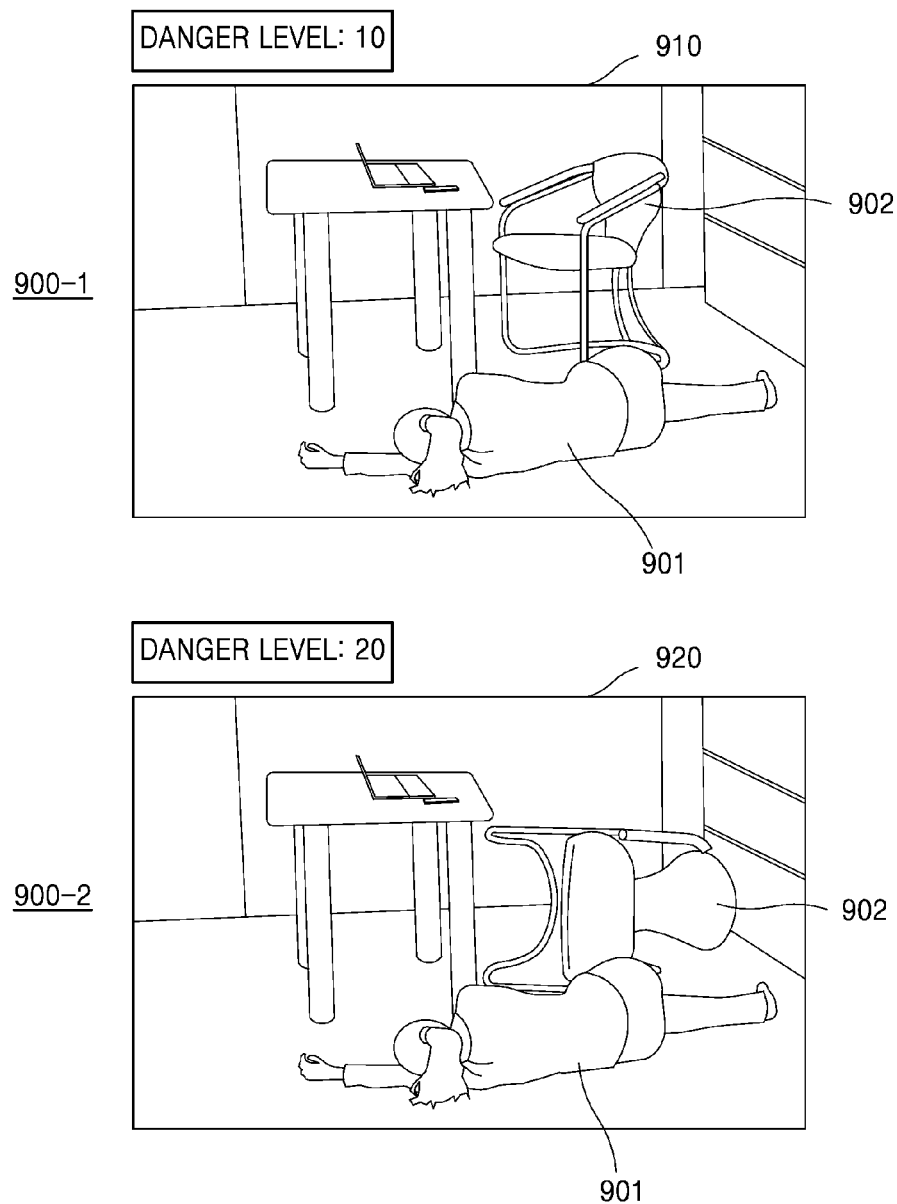
FIG. 9 is a view for explaining an operation of determining a danger level according to an embodiment.

FIG. 9 is a view for explaining an operation of determining a danger level according to an embodiment.

A case where a user falls in the office will be described in FIG. 9 as an example.

Referring to 900-1 of FIG. 9, the dangerous situation detection device 1000 may determine that a user 901 has fallen by using an appearance model and a motion model. The dangerous situation detection device 1000 may analyze at least one first image 910 obtained through the moving DVS 1100. The dangerous situation detection device 1000 may analyze the at least one first image 910 with an image obtained through an external camera. The dangerous situation detection device 1000 may obtain at least one detailed image or detailed information including information about the environment around the DVS 1100. The dangerous situation detection device 1000 may obtain the environmental information through a server, an external camera, a user input, and other sensors.

According to an embodiment, the dangerous situation detection device 1000 may recognize that there is no motion of the user 901 that has fallen through the first image 910 obtained through the moving DVS 1100. Furthermore, the dangerous situation detection device 1000 may determine that the material of a floor where the user 901 has fallen is a general floor mat, and the user 901 is wearing shoes, the user 901 is at least 1 m away from the desk, and the desk and chair 902 are not collapsed. The dangerous situation detection device 1000 may determine a danger level of the fall state as '10' by using information obtained as a result of analyzing the at least one first image 910 as a whole.

Referring to 900-2 of FIG. 9, the dangerous situation detection device 1000 may determine that the user 901 has fallen by using the appearance model and the motion model.

The chair 902 may be collapsed in the second image 920 unlike in the first image 910. The dangerous situation detection device 1000 may determine that a state of the user 901 is more dangerous when the chair 902 is collapsed with the user 901 compared to when only the user 901 falls. Accordingly, the dangerous situation detection device 1000 may determine a danger level of the fall state as '20'.

Figure 10:
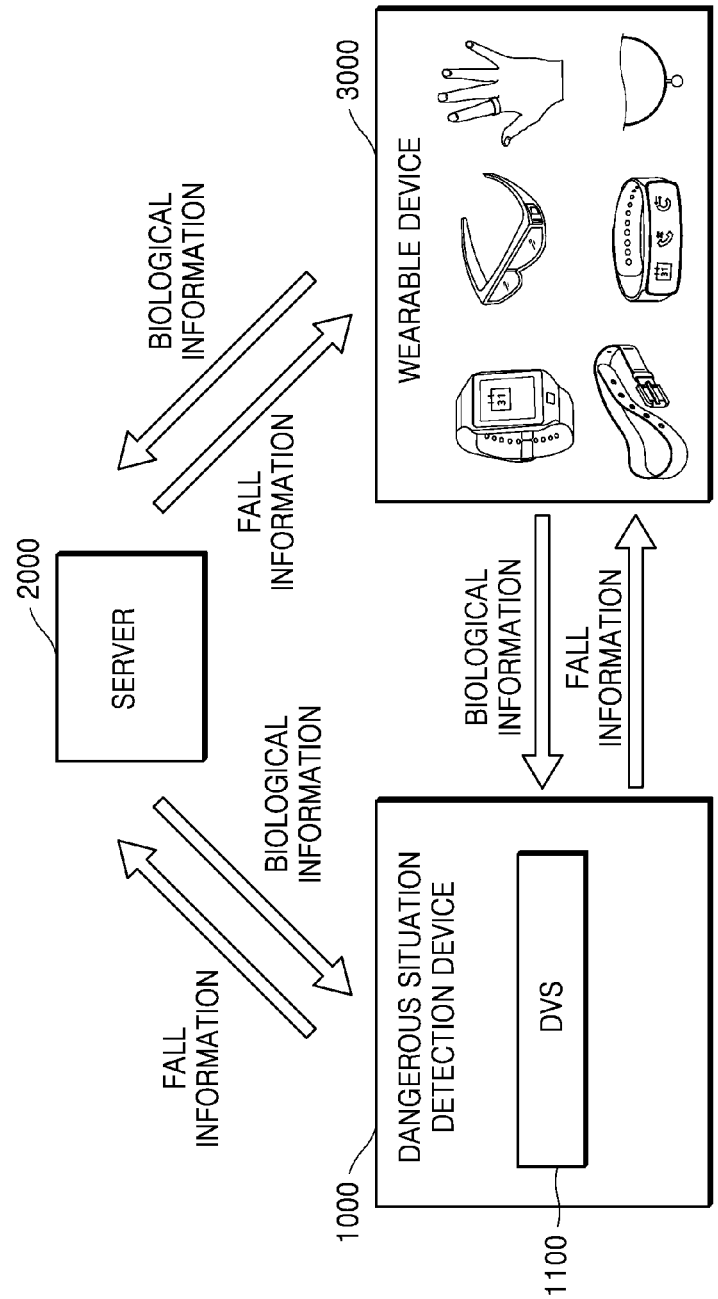
FIG. 10 is a view for explaining a system for analyzing a danger level of a fall state using biological information measured in a wearable device according to an embodiment.

FIG. 10 is a view for explaining a system for analyzing a danger level of a fall state using biological information measured in a wearable device according to an embodiment.

The system for analyzing the danger level of a fall state may include, but is not limited to, the dangerous situation detection device 1000, a server 2000, and a wearable device 3000. For example, when the dangerous situation detection device 1000 is in direct communication with the wearable device 3000, the system for analyzing the danger level of a fall state may not include the server 2000.

The wearable device 3000 may include, but is not limited to, at least one of an accessory type device (e.g., watches, rings, bracelets, braces, necklaces, glasses, or contact lenses), a head-mounted device (HMD), a textile or garment-integrated device (e.g., an electronic apparel), a body-attachment device (e.g., a skin pad), or an implantable device (e.g., an implantable circuit).

According to an embodiment, the dangerous situation detection device 1000 may obtain biological information of an object measured by the wearable device 3000 worn by the object when a state of the object is determined as a fall state. The dangerous situation detection device 1000 may receive the biological information directly from the wearable device 3000 or may receive the biological information through the server 2000.

According to an embodiment, the dangerous situation detection device 1000 may determine the danger level of a fall state using the biological information of the object. For example, when a heart rate is below a threshold value, when a blood pressure is equal to or greater than the threshold value, when the number of breaths is below the threshold value, when a body temperature is outside a critical range, or when the current time is night, the dangerous situation detection device 1000 may determine the danger level of a fall state to a high degree.

According to an embodiment, the server 2000 may receive fall information that a state of the object is a fall state from the dangerous situation detection device 1000, and may receive the biological information (e.g., blood pressure information, blood glucose information, heart rate information, body temperature information, etc.) of the object from the wearable device 3000. In this case, the server 2000 may determine a danger level of a fall state of the object using the fall information and the biological information. If the danger level of the fall state is greater than the threshold value, the server 2000 may send a warning message to an external device (e.g., a medical institution server, a user device of a user associated with the object, a server of an emergency services unit, and/or the like). According to an embodiment, the server 2000 may send information about the danger level of the fall state to the dangerous situation detection device 1000 or the wearable device 3000.

According to an embodiment, the wearable device 3000 may receive fall information indicating that the state of the object is a fall state from the dangerous situation detection device 1000 or the server 2000. The wearable device 3000 may determine the danger level of the fall state of the object by using the biological information of the object measured in the wearable device 3000. If the danger level of the fall state is greater than the threshold value, the wearable device 3000 may send a warning message to an external device (e.g., a medical institution server). Furthermore, according to an embodiment, the server 2000 may send information about the danger level of the fall state to the dangerous situation detection device 1000 or the wearable device 3000.

Figure 11:
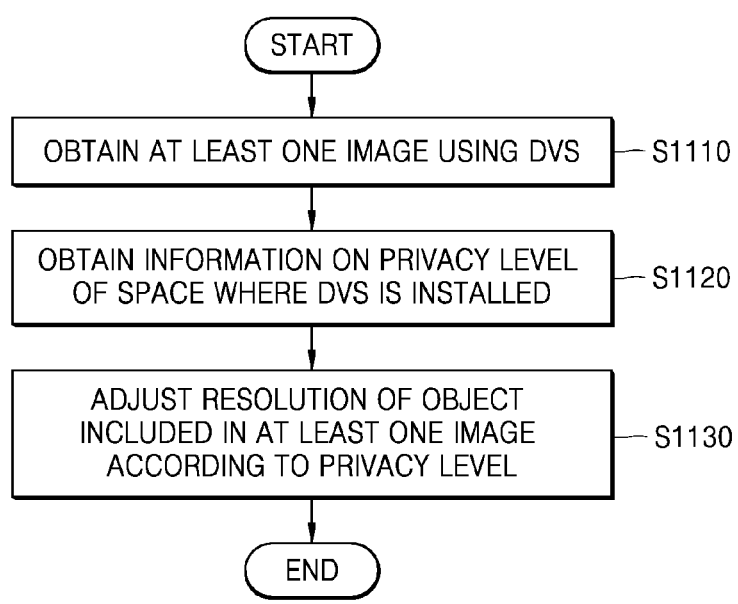
FIG. 11 is a flowchart illustrating a method of adjusting resolution of an object according to a privacy level according to an embodiment.

FIG. 11 is a flowchart illustrating a method of adjusting resolution of an object according to a privacy level according to an embodiment.

In operation S1110, the dangerous situation detection device 1000 may obtain at least one image using the DVS 1100.

In operation S1120, the dangerous situation detection device 1000 may obtain information on a privacy level of a space where the DVS 1100 is installed.

According to an embodiment, the dangerous situation detection device 1000 may receive the privacy level from a user when DVS 1100 is installed. According to an embodiment, the dangerous situation detection device 1000 may obtain information on a predefined privacy level from the server 2000.

For example, the privacy level may be set very high for a bathroom or toilet, relatively high for a dress room or bedroom, and relatively low for a living room, kitchen, and staircase.

In operation S1130, the dangerous situation detection device 1000 may adjust resolution of the object included in at least one image according to the privacy level. For example, the higher the privacy level of the space including at least one image, the lower the resolution of the object. The lower the privacy level of the space including at least one image, the higher the resolution of the object.

Figure 12:
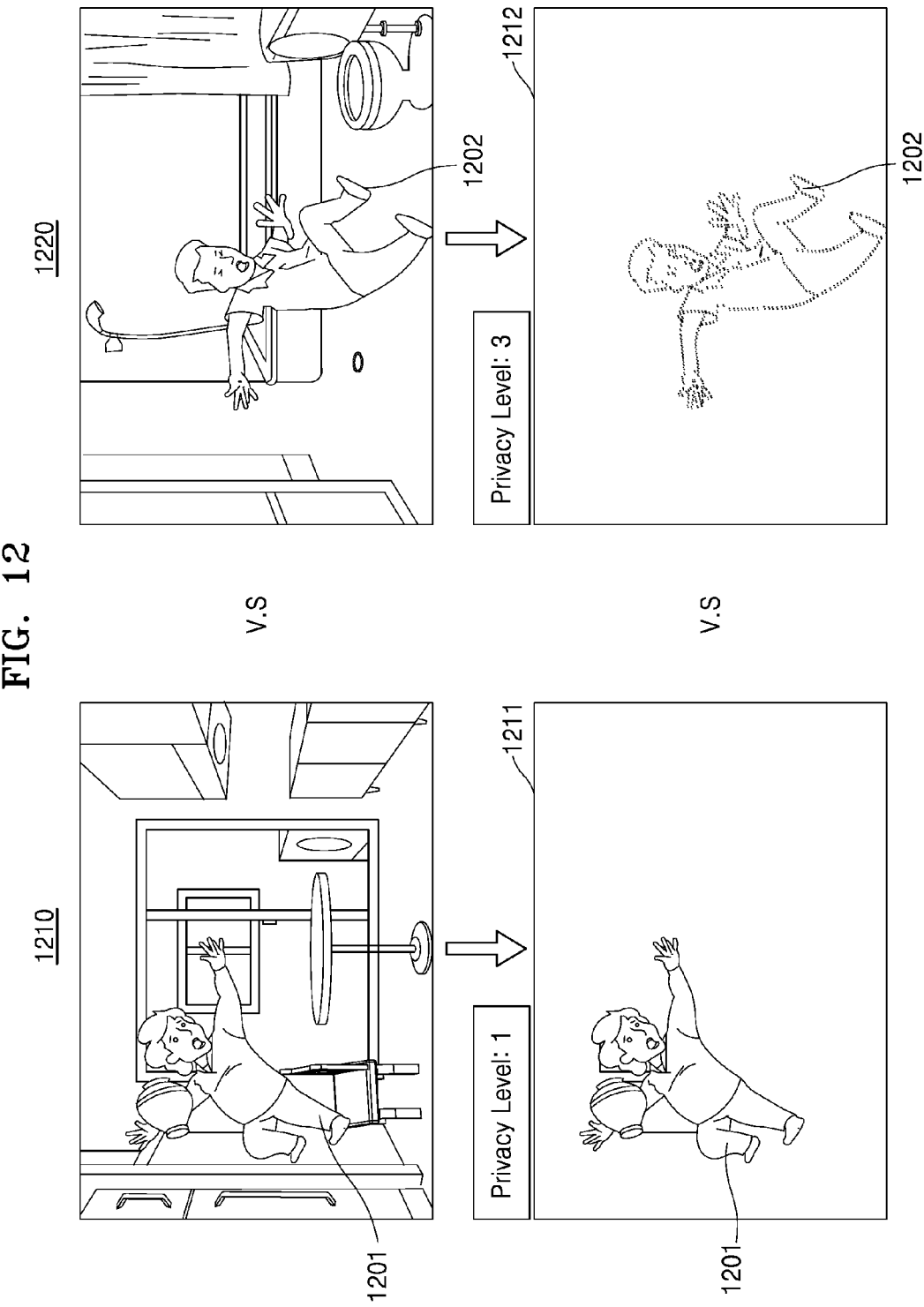
FIG. 12 is a view for explaining an operation of adjusting resolution of an object according to a privacy level according to an embodiment.

FIG. 12 is a view for explaining an operation of adjusting resolution of an object according to a privacy level according to an embodiment.

Referring to 1210 of FIG. 12, a first user 1201 may fall in the kitchen. The dangerous situation detection device 1000 may obtain an image 1211 of the falling first user 1201 by using the DVS 1100. The dangerous situation detection device 1000 may confirm a privacy level of the kitchen in which the first user 1201 is located and may express an outline of the first user 1201 with resolution corresponding to the confirmed privacy level. For example, since the privacy level of the kitchen is '1', which is a general level, the dangerous situation detection device 1000 may express the outline of the first user 1201 with general resolution.

Referring to 1220 of FIG. 12, a second user 1202 may fall in the toilet. The dangerous situation detection device 1000 may obtain an image 1212 of the falling second user 1202 using the DVS 1100. The dangerous situation detection device 1000 may confirm a privacy level of the toilet in which the second user 1202 is located and may express an outline of the second user 1202 with resolution corresponding to the confirmed privacy level. For example, since the privacy level of the toilet is '3', which is a very high level, the dangerous situation detection device 1000 may express the outline of the second user 1202 with low resolution.

Figure 13:
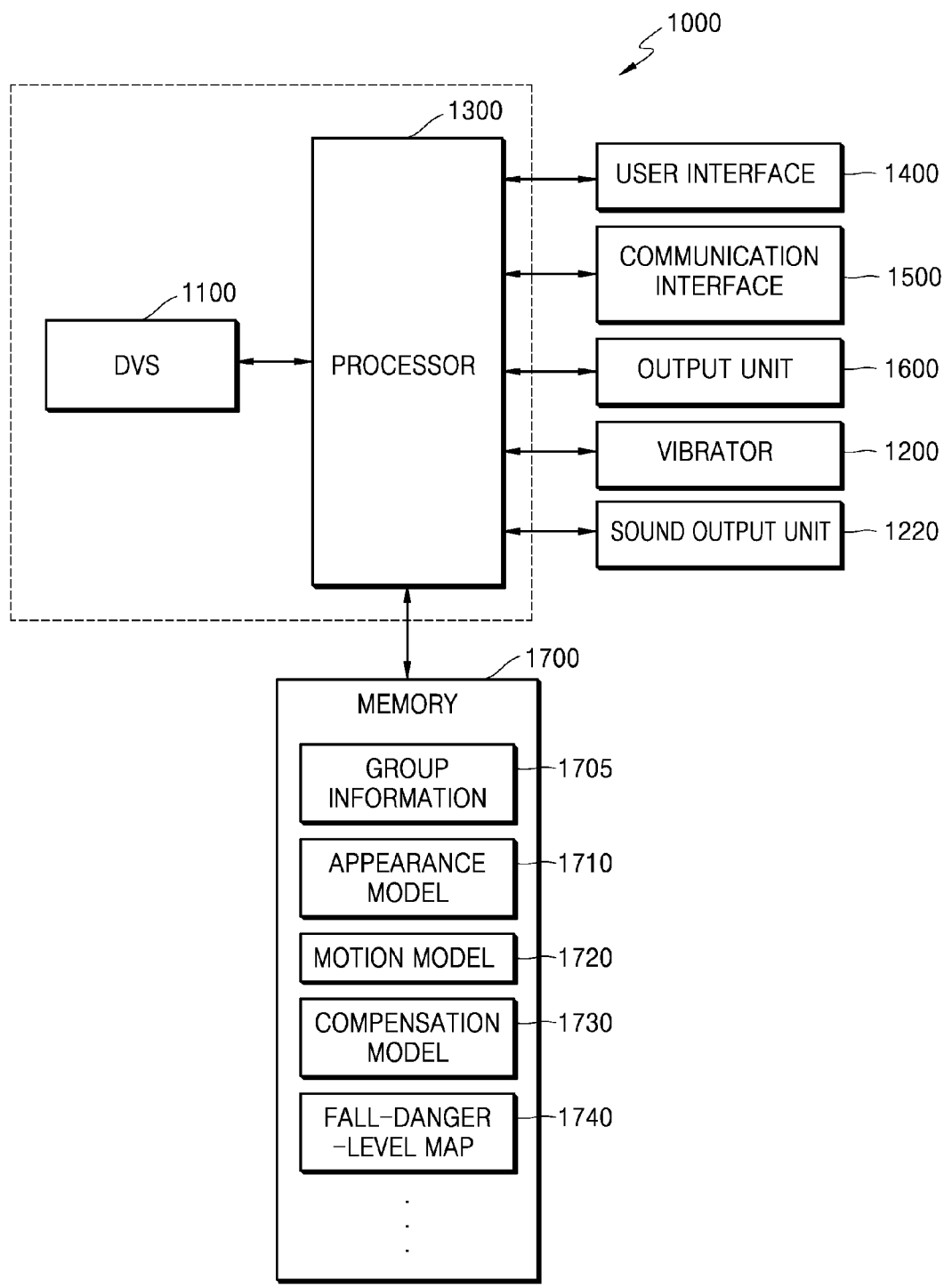
FIG. 13 is a block diagram illustrating a configuration of a fall detection device according to an embodiment.

FIG. 13 is a block diagram illustrating a configuration of a fall detection device according to an embodiment.

As illustrated in FIG. 13, the dangerous situation detection device 1000 according to an embodiment may include the DVS 1100 and a processor 1300. The dangerous situation detection device 1000 may be implemented by using more or less elements than those shown in FIG. 13. For example, the dangerous situation detection device 1000 may further include a user interface 1400, a communication interface 1500, an output unit 1600, and a memory 1700 in addition to the DVS 1100, the processor 1300, and the like.

Hereinafter, the components will be sequentially described.

The DVS 1100 may include an image sensor that adopts a method of receiving information of a person's iris and is a sensor capable of obtaining image data of a moving object. For example, the DVS 1100 may transmit image data to the processor 1300 only when there is a local change by motion in pixel units. That is, the DVS 1100 may transmit image data to the processor 1300 only when a motion event occurs. Accordingly, the DVS 1100 might not process data when an object is stopped, and instead might capture a moving object only when the object moves, and may transmit the data to the processor 1300.

The processor 1300 may typically control general operations of the dangerous situation detection device 1000. For example, the processor 1300 may control the DVS 1100, a vibrator 1200, the user interface 1400, the communication interface 1500, and the output unit 1600 by executing programs stored in the memory 1700.

According to an embodiment, the processor 1300 may analyze at least one image obtained from the DVS 1100 to analyze profile information of the object. The processor 1300 may retrieve setting information of a group that best matches the analyzed profile information of the object. The processor 1300 may match the object and the group. The processor 1300 may determine a dangerous situation of the object based on the setting information of the matched group.

According to an embodiment, the processor 1300 may detect an image including an object of a predefined posture from at least one image obtained by the DVS 1100. The predefined posture may be a posture related to a fall. For example, the predefined posture may be a posture where some (e.g., back, stomach, head, etc.) or all of the body touches the floor. For example, when motion of the object is detected, the processor 1300 may compare the posture of the object included in the at least one image with the predefined posture to detect an image including the object of the predefined posture.

The processor 1300 may determine, based on information about a first motion change of the object, whether a state of the object is a fall state. For example, the processor 1300 may determine the state of the object as a fall state if a degree of similarity between the first motion change of the object and a second motion change representing a pre-stored fall is greater than a threshold value. The pre-stored fall may be a value set differently according to the setting information of the group.

The processor 1300 may obtain information about the environment around the object or fall type information of the object, and may use time and space environmental information or the fall type information to determine a danger level of a fall state. According to an embodiment, the processor 1300 may send a warning message to an external device through the communication interface 1500 when the danger level of a fall state is greater than the threshold value.

The processor 1300 may detect motion of the object after the state of the object is determined as a fall state, and may adjust a danger level of the fall state upward when the motion of the object is less than the threshold value for a certain period of time.

The processor 1300 may detect a fall of the object using a deep learning model pre-stored in the memory 1700 or using a deep learning model received from the outside. Furthermore, the processor 1300 may also directly generate a deep running model for detecting a fall.

The user interface 1400 may include a device for a user to input data for controlling the dangerous situation detection device 1000. For example, the user interface 1400 may include, but is not limited to, a keypad, a dome switch, a touch pad (a touch capacitive type touch pad, a pressure resistive type touch pad, an infrared beam sensing type touch pad, a surface acoustic wave type touch pad, an integral strain gauge type touch pad, a Piezo effect type touch pad, or the like), a jog wheel, a jog switch and the like, but is not limited thereto.

The user interface 1400 may receive an input of setting a privacy level of a space where the DVS 1100 is installed. Alternatively, the user interface 1400 may receive an input of setting resolution of an image obtained by the DVS 1100. In addition, the user interface 1400 may receive a user input of directly inputting a user profile.

The communication interface 1500 may include one or more components that enable communication between the dangerous situation detection device 1000 and the server 2000, between the dangerous situation detection device 1000 and the wearable device 3000, between the dangerous situation detection device 1000 and a mobile terminal, and/or between the dangerous situation detection device 1000 and another device. For example, the communication interface 1500 may include a short-range communication unit, a mobile communication unit, and the like.

The short-range wireless communication unit may include, but is not limited to, a Bluetooth communication part, a Bluetooth Low Energy (BLE) communication part, a near field wireless communication part, a wireless local area network (WLAN) communication part, a ZigBee communication part, an infrared Data Association (IrDA) communication part, a Wi-Fi Direct (WFD) communication part, an ultra wideband (UWB) communication part, or an Ant+ communication part.

The mobile communication unit transmits and receives wireless signals to and from at least one selected from a base station, an external terminal, and a server on a mobile communication network. Here, the wireless signal may be a voice call signal, a video call signal, or data in any one of various formats according to transmission and reception of a text/multimedia message. The mobile communication unit may use at least one of 5G, long-term evolution (LTE), LTE advance (LTE-A), code division multiple access (CDMA), wideband CDMA (WCDMA), a universal mobile telecommunications system (UMTS), a wireless broadband (Wi-Bro), and a global system for mobile communications (GSM).

The output unit 1600 is configured to output a video signal, an audio signal, or a vibration signal. The output unit 1600 may include a display unit, a sound output unit, a vibration motor, and the like.

The display unit may display information processed by the dangerous situation detection device 1000. For example, the display unit may display an image obtained by the DVS 1100, a preview image, a video file list, a video playback screen, and the like.

When the display unit and a touch pad have a layer structure and are configured as a touch screen, the display unit may be used as an input device in addition to an output device. The display unit may include at least one of a liquid crystal display (LCD), a thin film transistor-LCD (TFT-LCD), an organic light-emitting diode (OLED) display, a flexible display, a 3D display, and an electrophoretic display.

The sound output unit 1220 outputs audio data that is received from the communication interface 1500 or stored in the memory 1700. Furthermore, the sound output unit 1220 outputs a sound signal related to a function (e.g., generating a warning message) performed in the dangerous situation detection device 1000. The sound output unit 1220 may include a speaker, a buzzer, and the like.

The memory 1700 may store one or more programs for processing and controlling the processor 1300 and may store input/output data (e.g., static images, videos, etc.).

The memory 1700 may include, for example, an internal memory or an external memory. The internal memory may include, for example, at least one of a volatile memory (e.g., dynamic random access memory (DRAM), static random access memory (SRAM), synchronous DRAM (SDRAM), or the like), a nonvolatile memory (e.g., one-time programmable read-only memory (OTPROM), programmable ROM (PROM), erasable and programmable ROM (EPROM), electrically erasable and programmable ROM (EEPROM), mask ROM, flash ROM, or the like), a flash memory (e.g., a NAND flash memory or NOR flash memory), a hard-disk drive (HDD), and a solid-state drive (SSD).

The external memory may include a flash drive, for example, compact flash (CF), secure digital (SD), micro secure digital (micro-SD), mini secure digital (mini-SD), extreme digital (xD), and a memory stick. The external memory may be functionally and/or physically connected to the dangerous situation detection device 1000 through various interfaces.

In addition, the dangerous situation detection device 1000 may operate a web storage that performs a storage function of the memory 1700 on the Internet.

Programs stored in the memory 1700 may be classified into a plurality of modules according to their functions, for example, group information 1705, the appearance model 1710, a motion model 1720, a compensation model 1730, and the like. According to an embodiment, the memory 1700 may include a fall-danger-level module 1740 that stores the fall-danger-level map 600.

The group information 1705 may store information on a plurality of groups classified according to a user profile. The plurality of groups includes information used as reference information for determining a dangerous situation of an object. The plurality of groups may be classified based on personal identification information such as gender, age, lesion, walking speed, and stride of a user.

The appearance model 1710 may be a model that is trained to detect a body shape or pose of an object included in each of the static images by analyzing static images one by one and determine whether the detected body shape or pose of the object is similar to a predefined posture related to a fall.

The motion model 1720 may be a model that is trained to detect motion patterns of an object by analyzing a plurality of images (e.g., videos), and determine whether the detected motion patterns of the object are similar to a motion pattern indicating a fall. Generally, since the motion model 1720 processes multiple images in a cumulative manner (e.g., N images stacking), the processing takes N times longer than in the appearance model 1710 that processes a single image.

The compensation model 1730 may be a trained model to compensate for a size, shape, or occlusion of an object included in an image obtained by the DVS 1100.

A fall-danger-level module 1740 may be a map indicating an area that may be dangerous when a fall occurs.

Figure 14:
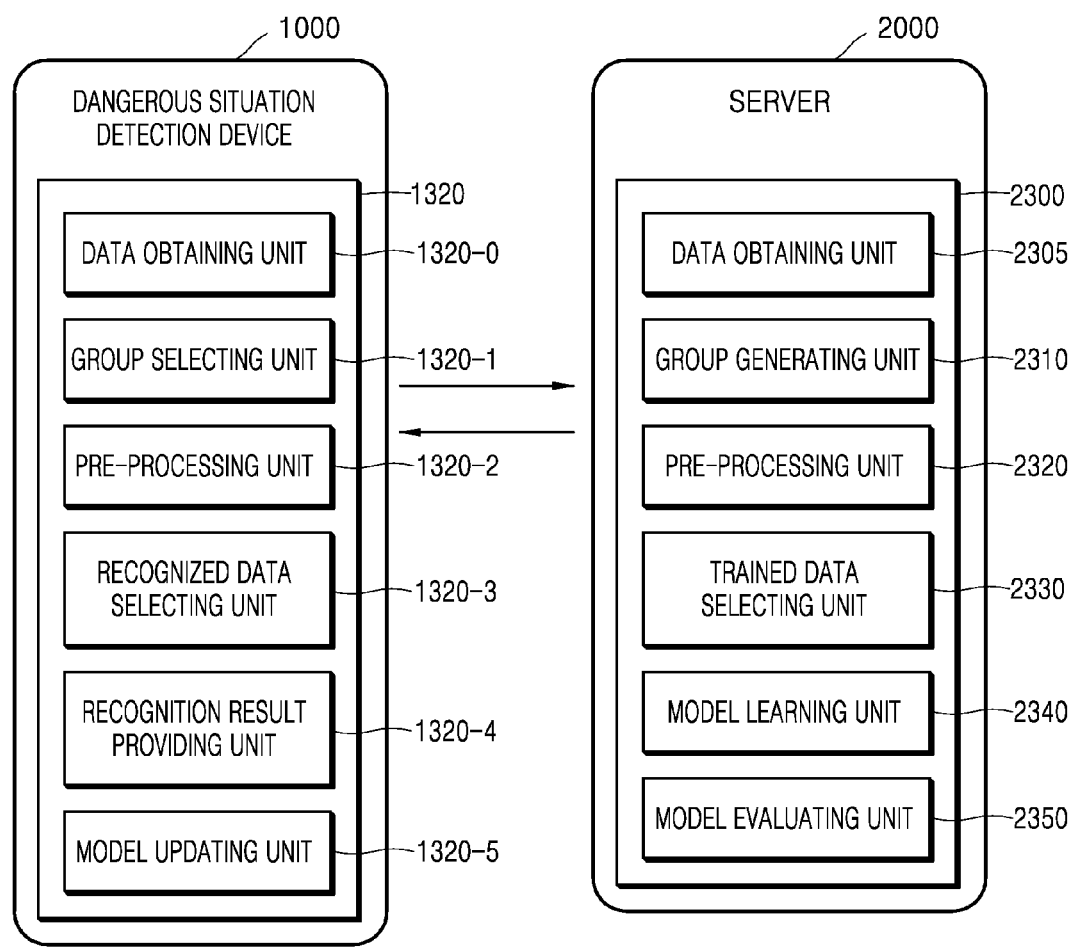
FIG. 14 is a view illustrating an example in which a fall detection device and a server work together to learn and recognize data, according to an embodiment.

FIG. 14 is a view illustrating an example in which a fall detection device and a server work together to learn and recognize data, according to an embodiment.

Referring to FIG. 14, the server 2000 may learn a reference for determining a fall state, and the dangerous situation detection device 1000 may determine the fall state based on a learning result of the server 2000.

As shown in FIG. 14, the dangerous situation detection device 1000 may include a processor 1320 including a data obtaining unit 1320-0, a group selecting unit 1320-1, a pre-processing unit 1320-2, a recognized data selecting unit 1320-4, and a model updating unit 1320-5. As further shown in FIG. 14, the server 2000 may include a processor 2300 including a data obtaining unit 2305, a group generating unit 2310, a pre-processing unit 2320, a trained data selecting unit 2330, a model learning unit 2340, and a model evaluating unit 2350.

The group generating unit 2310 of the server 2000 may generate a plurality of groups based on a user profile. Each of the plurality of groups may include group setting information. The group setting information may include information about a model that is personalized by the user profile. The group setting information may be used as reference information for determining a dangerous situation of an object detected by the dangerous situation detection device 1000 thereafter.

The group selecting unit 1320-1 of the dangerous situation detection device 1000 may select a group most similar to object information from among the plurality of groups based on motion information of the object.

In this case, the model learning unit 2340 of the server 2000 may perform a function of a data learning unit. The model learning unit 2340 of the server 2000 may learn what data to use to determine the fall state and how to determine the fall state using the data. The model learning unit 2340 may obtain data to be used for learning and apply the obtained data to a data recognition model to be described later below, so that the model learning unit 2340 may learn a reference for situation determination.

Also, the recognition result providing unit 1320-4 of the dangerous situation detection device 1000 may determine the situation by applying data selected by the recognized data selecting unit 1320-3 to the data recognition model generated by the server 2000. For example, the recognition result providing unit 1320-4 may transmit the data selected by the recognized data selecting unit 1320-3 to the server 2000, and may request the server 2000 to apply the data selected by the recognized data selecting unit 1320-3 to the data recognition model to determine the situation. Furthermore, the recognition result providing unit 1320-4 may receive information on the situation determined by the server 2000 from the server 2000.

Alternatively, the recognition result providing unit 1320-4 of the dangerous situation detection device 1000 may receive the data recognition model generated by the server 2000 from the server 2000, and may determine the fall state using the received data recognition model. In this case, the recognition result providing unit 1320-4 of the dangerous situation detection device 1000 may determine the fall state by applying the data selected by the recognized data selecting unit 1320-3 to the data recognition model received from the server 2000.

The method according to an embodiment may be implemented as program commands, i.e., software (e.g., a program) containing one or more instructions that are stored in a machine (e.g., a computer)-readable storage medium (e.g., internal memory) or external memory and which can be executed by various computer devices, and recorded on a computer-readable medium. The computer-readable medium may include programs, data files, data structures or a combination thereof. Programs recorded on the medium may be particularly designed and structured for the present disclosure or available to those of skill in computer software. Examples of the computer-readable recording medium include magnetic media, such as a hard disc, a floppy disc, and a magnetic tape; optical media, such as a compact disc-read only memory (CD-ROM) and a digital versatile disc (DVD); magneto-optical media, such as floptical discs; a ROM; a RAM; and a flash memory. The one or more instructions may contain a code made by a compiler or a code executable by an interpreter.

The one or more embodiments may be embodied as computer readable code/instructions on a recording medium, e.g., a program module to be executed in computers, the program module including computer-readable instructions. A non-transitory computer readable medium may be any usable medium that may be accessed by a computer, and may include any usable medium, such as, a volatile and non-volatile medium and a discrete type and non-discrete type medium. Also, the non-transitory computer readable medium may include all computer storing media and communication media. The computer storing medium may include any medium, such as, a volatile and non-volatile medium and a discrete type and non-discrete type medium that is realized by a method or technique for storing information, such as, a computer readable instruction, a data structure, a program module, or other data. The communication medium may include other data of modulated signal, such as, a computer readable instruction, a data structure, a program module, or a carrier signal, or other transmission mechanism, and an arbitrary information medium. Furthermore, some embodiments may also be implemented as a computer program or a computer program product, which includes instructions executable by a computer.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of detecting a dangerous situation, the method comprising:
   obtaining, by a device and from a dynamic vision sensor (DVS), a set of images of an object;
   determining, by the device, a group to which the object belongs based on an attribute of the object and an attribute of the group;
   analyzing, by the device, the set of images of the object to obtain information associated with a change in motion of the object for a time frame;
   determining, by the device, that the object has fallen based on the information associated with the change in motion of the object for the time frame;
   determining, by the device, that the object is associated with the dangerous situation based on determining that the object has fallen; and
   determining, by the device, a danger level associated with the dangerous situation based on the change in motion of the object being less than a threshold value for the time frame, and based on setting information associated with the group to which the object belongs,
   wherein the setting information is determined based on profile information associated with users of the group.

2. The method of claim 1, further comprising:
   generating information associated with the group based on the profile information for the users having similar attributes to the object; and
   determining the setting information associated with the group based on the generating the information associated with the group.

3. The method of claim 2, wherein the profile information indicates a gender, an age, a lesion, a normal activity, a walking speed, an activity pattern, a stride, and whether an auxiliary device is installed.

4. The method of claim 1, further comprising:
   determining the group to which the object belongs using a learning network model driven by an artificial intelligence (AI) engine.

5. The method of claim 1, further comprising:
   updating the setting information associated with the group to which the object belongs by analyzing at least one image, from among the set of images, of the object obtained from the DVS.

6. The method of claim 1, further comprising:
   obtaining user profile information comprising the attribute of the object from an external device;
   determining that a similarity between the attribute of the object and the attribute of the group satisfies a threshold; and
   determining the group to which the object belongs based on the similarity between the attribute of the object and the attribute of the group satisfying the threshold.

7. The method of claim 1, further comprising:
obtaining an image comprising the information associated with a surrounding environment of the DVS; and
determining the danger level associated with the dangerous situation based on the image comprising the information associated with the surrounding environment of the DVS.

8. The method of claim 1, further comprising:
comparing a posture of the object and a predetermined posture,
wherein the determining that the object has fallen comprises determining that the object has fallen based on comparing the posture of the object and the predetermined posture.

9. The method of claim 1, wherein the obtaining the set of images comprises:
adjusting a resolution of the set of images based on a privacy level of a space where the DVS is installed.

10. A dangerous situation detection device comprising:
a dynamic vision sensor (DVS) configured to obtain a set of images of an object;
a memory configured to store one or more instructions; and
a processor configured to execute the one or more instructions to:
determine a group to which the object belongs based on an attribute of the group and an attribute of the object;
analyze the set of images of the object to obtain information associated with a change in motion of the object for a time frame;
determine, based on the set of images, that the object has fallen based on the information associated with the change in motion of the object for the time frame;
determine that the object is associated with a dangerous situation based on determining that the object has fallen; and
determine a danger level associated with the dangerous situation based on the change in motion of the object being less than a threshold value for the time frame, and based on setting information associated with the group to which the object belongs,
wherein the setting information is determined based on profile information associated with users of the group.

11. The dangerous situation detection device of claim 10, wherein the processor is further configured to:
identify the profile information associated with the users of the group; and
determine the setting information based on the profile information.

12. The dangerous situation detection device of claim 11, wherein the profile information indicates a gender, an age, a lesion, a normal activity, a walking speed, an activity pattern, a stride, and whether an auxiliary device is installed.

13. The dangerous situation detection device of claim 10, wherein the processor is further configured to determine the group to which the object belongs by using a learning network model driven by an artificial intelligence (AI) engine.

14. The dangerous situation detection device of claim 10, wherein the processor is further configured to:
update the setting information associated with the group to which the object belongs based on the set of images obtained from the DVS.

15. The dangerous situation detection device of claim 10, wherein the processor is further configured to:
determine that a similarity between the attribute of the group and the attribute of the object satisfies a threshold; and
determine the group to which the object belongs based on the similarity between the attribute of the object and the attribute of the group satisfying the threshold.

16. A computer program product comprising a computer readable storage medium comprising instructions that, when executed by one or more processors, cause the one or more processors to:
obtain, from a dynamic vision sensor (DVS), a set of images of an object;
determine a group to which the object belongs based on an attribute of the object and an attribute of the group;
analyze the set of images of the object to obtain information associated with a change in motion of the object for a time frame;
determine that the object has fallen based on the information associated with the change in motion of the object for the time frame;
determine that the object is in a dangerous situation based on determining that the object has fallen; and
determine a danger level associated with the dangerous situation based on the change in motion of the object being less than a threshold value for the time frame, and based on setting information associated with the group to which the object belongs,
wherein the setting information is determined based on profile information associated with users of the group.

* * * * *